(12) United States Patent
Lee et al.

(10) Patent No.: US 11,607,131 B2
(45) Date of Patent: Mar. 21, 2023

(54) APPARATUS FOR MEASURING IMPLANT OSSEOINTEGRATION

(71) Applicant: UNIVERSITY INDUSTRY FOUNDATION, YONSEI UNIVERSITY WONJU CAMPUS, Wonju-si (KR)

(72) Inventors: Yong Heum Lee, Wonju-si (KR); Soo Byeong Kim, Ansan-si (KR); Na Ra Lee, Gimhae-si (KR)

(73) Assignee: UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 1062 days.

(21) Appl. No.: 16/311,983

(22) PCT Filed: May 23, 2017

(86) PCT No.: PCT/KR2017/005352
§ 371 (c)(1),
(2) Date: Dec. 20, 2018

(87) PCT Pub. No.: WO2017/222194
PCT Pub. Date: Dec. 28, 2017

(65) Prior Publication Data
US 2019/0192003 A1 Jun. 27, 2019

(30) Foreign Application Priority Data
Jun. 21, 2016 (KR) .................. 10-2016-0077251

(51) Int. Cl.
*A61B 5/00* (2006.01)
*A61C 19/04* (2006.01)
(Continued)

(52) U.S. Cl.
CPC .......... *A61B 5/0051* (2013.01); *A61B 5/4504* (2013.01); *A61B 5/4848* (2013.01);
(Continued)

(58) Field of Classification Search
CPC ..... A61B 5/0051; A61B 5/4851; A61B 5/682; A61C 19/04; A61C 8/00
See application file for complete search history.

(56) References Cited

U.S. PATENT DOCUMENTS

| 6,918,763 B2 | 7/2005 | Huang et al. | |
| 2008/0199828 A1* | 8/2008 | Pan .................. | G01N 29/4454 433/167 |
| 2013/0122458 A1* | 5/2013 | Pan .................. | A61B 8/0875 433/119 |

FOREIGN PATENT DOCUMENTS

| JP | 2003524475 | 8/2003 |
| KR | 20110074949 | 7/2011 |

(Continued)

OTHER PUBLICATIONS

English translation of JP 2003524475 (Year: 2003).*
International Search Report—PCT/KR2017/005352 dated Sep. 1, 2017.

*Primary Examiner* — Alex M Valvis
*Assistant Examiner* — Yasmeen S Warsi
(74) *Attorney, Agent, or Firm* — Cantor Colburn LLP

(57) ABSTRACT

Provided is an apparatus for measuring implant osseointegration, and the apparatus for measuring implant osseointegration includes: a vibration generation unit configured to apply multiple vibrations with frequencies in different bands, respectively, to an implant fixture; a vibration sensor configured to measure three-axis vibration information of the implant fixture caused by the vibrations from the vibra- (Continued)

tion generation unit; and a control unit configured to determine the degree of osseointegration based on the measured vibration information.

6 Claims, 3 Drawing Sheets

(51) Int. Cl.
    *A61C 8/02*           (2006.01)
    *A61C 8/00*           (2006.01)

(52) U.S. Cl.
    CPC .......... *A61B 5/4851* (2013.01); *A61C 8/0006* (2013.01); *A61C 19/04* (2013.01); *A61B 5/682* (2013.01); *A61B 5/7253* (2013.01); *A61B 2505/05* (2013.01); *A61B 2505/09* (2013.01); *A61B 2562/0219* (2013.01); *A61C 8/00* (2013.01)

(56) References Cited

FOREIGN PATENT DOCUMENTS

| | | |
|---|---|---|
| KR | 20110075170 | 7/2011 |
| KR | 101272253 | 6/2013 |
| KR | 20150047468 | 5/2015 |
| WO | 2015048908 | 4/2015 |

* cited by examiner

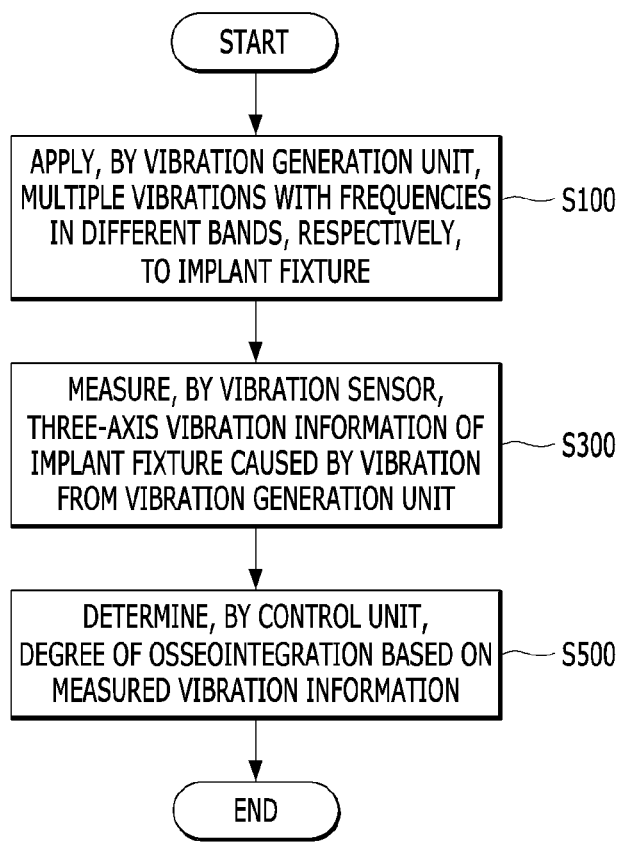

APPARATUS FOR MEASURING IMPLANT OSSEOINTEGRATION

TECHNICAL FIELD

The present disclosure relates to an apparatus for measuring implant osseointegration.

BACKGROUND

In general, an implant operation has a process of inserting and integrating an implant (dental implant) into bone where a natural tooth once was and fixing an artificial tooth to the implant integrated into the bone. Therefore, during the implant operation, the integration between the implant and the bone is essential, and the initial stability of the implant is an important criterion for determining osseointegration. Accordingly, the initial stability of the implant should be measured when the implant is inserted.

As conventional measurement technologies for monitoring and quantitatively accurately measuring the status of an implant, percussion response, radiographic inspection, Periotest, Dental Fine Tester, removal torque measurement, resonant frequency analysis, etc. have been suggested in the existing treatises, and research studies have continued to develop an apparatus for measuring implant osseointegration with more accuracy than the conventional technologies.

The background technology of the present disclosure is disclosed in Korean Patent Laid-open Publication No. 10-2011-0074949.

DISCLOSURE OF THE INVENTION

Problems to be Solved by the Invention

The present disclosure is conceived to solve the above-described problem of the conventional technologies and provides an apparatus for measuring implant osseointegration and a method for measuring implant osseointegration with improved accuracy compared to the conventional ones.

However, problems to be solved by the present disclosure are not limited to the above-described problems. There may be other problems to be solved by the present disclosure.

Means for Solving the Problems

As a technical means for solving the above-described technical problems, an apparatus for measuring implant osseointegration according to a first aspect of the present disclosure may include: a vibration generation unit configured to apply multiple vibrations with frequencies in different bands, respectively, to an implant fixture; a vibration sensor configured to measure three-axis vibration information of the implant fixture caused by the vibrations from the vibration generation unit; and a control unit configured to determine the degree of osseointegration based on the measured vibration information.

A method for measuring implant osseointegration according to a second aspect of the present disclosure may include: applying, by a vibration generation unit, multiple vibrations with frequencies in different bands, respectively, to an implant fixture; measuring, by a vibration sensor, three-axis vibration information of the implant fixture caused by the vibrations from the vibration generation unit; and determining, by a control unit, the degree of osseointegration based on the measured vibration information.

The above-described embodiments are provided by way of illustration only and should not be construed as liming the present disclosure. Besides the above-described embodiments, there may be additional embodiments described in the accompanying drawings and the detailed description.

Effects of the Invention

According to the above-described means for solving the problems, multiple vibrations with frequencies in different bands, respectively, are applied to an implant fixture to measure three-axis (x-axis, y-axis, z-axis) vibration information of the implant fixture and the degree of osseointegration is determined based on the measured three-axis vibration information, and, thus, the accuracy of the degree of osseointegration can be improved.

BRIEF DESCRIPTION OF THE DRAWINGS

FIG. 3 is a schematic flowchart provided to explain a method for measuring implant osseointegration according to an embodiment of the present disclosure.

BEST MODE FOR CARRYING OUT THE INVENTION

Figure 1:
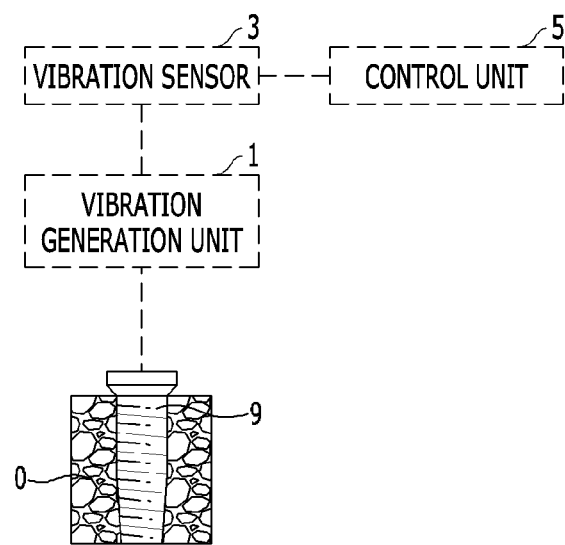
FIG. 1 is a schematic diagram provided to explain an apparatus for measuring implant osseointegration according to an embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the terms "on", "above", "on an upper end", "below", "under", and "on a lower end" that are used to designate a position of one element with respect to another element include both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Hereinafter, an apparatus for measuring implant osseointegration according to an embodiment of the present disclosure (hereinafter, referred to as "the present implant osseointegration measuring apparatus") will be described.

FIG. 1 is a schematic diagram provided to explain the present implant osseointegration measuring apparatus.

Referring to FIG. 1, the present implant osseointegration measuring apparatus includes a vibration generation unit 1. For example, the vibration generation unit 1 may include a small-sized vibration motor.

The vibration generation unit 1 can be attached to and detached from (installed in and removed from) an implant fixture 9. For example, referring to FIG. 1, the vibration generation unit 1 can be attached to and detached from an exposed portion of the implant fixture 9 inserted into alveolar bone 0. Therefore, the present implant osseointegration measuring apparatus may have a shape easy to be attached to and detached from the implant fixture 9.

The vibration generation unit 1 installed in the implant fixture 9 applies multiple vibrations with frequencies in different bands, respectively, to the implant fixture 9.

For example, the multiple vibrations with frequencies in different bands, respectively, may be low-frequency vibrations, medium-frequency vibrations, and high-frequency vibrations. For example, the low-frequency vibrations may be vibrations with frequencies of from 1,200 rpm to 3,600 rpm. Further, the medium-frequency vibrations may be vibrations with frequencies of from 4,200 rpm to 12,000 rpm. Furthermore, the high-frequency vibrations may be vibrations with frequencies of from 15,000 rpm to 24,000 rpm.

Further, referring to FIG. 1, the present implant osseointegration measuring apparatus includes a vibration sensor 3. The vibration sensor 3 measures three-axis vibration information of the implant fixture 9 caused by the vibrations from the vibration generation unit 1. In other words, the vibration sensor 3 may be a three-axis vibration sensor.

If the degree of osseointegration is determined by measuring only uniaxial vibration information of the implant fixture 9, the accuracy of the determined degree of osseointegration may be low. More specifically, when the implant fixture 9 vibrates, higher vibrations may be generated from other axes than an axis from which vibration information is measured. Therefore, if vibration information of an axis is measured, the degree of osseointegration is determined without consideration of vibration information of the other axes that generate higher vibrations, and, thus, the accuracy in determining the degree of osseointegration may be low.

However, the present implant osseointegration measuring apparatus measures three-axis (x-axis, y-axis, z-axis) vibration information of the implant fixture 9 and determines the degree of osseointegration based on the three-axis vibration information and thus can improve the accuracy compared to an apparatus configured to determine the degree of osseointegration only based on vibration information of a single axis.

As described above, the present implant osseointegration measuring apparatus may be an apparatus in which the vibration generation unit 1 and the vibration sensor 3 are built and modularized.

Figure 2:
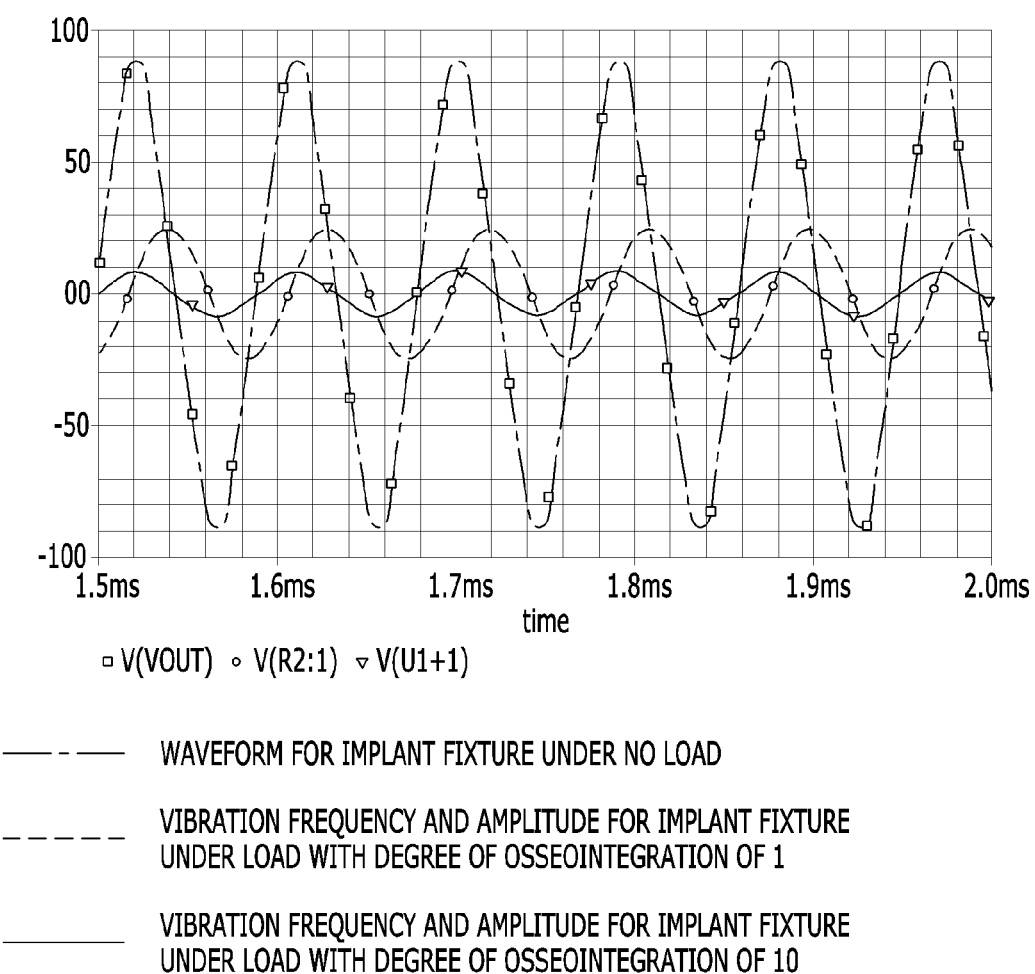
FIG. 2 is a graph showing waveforms measured by a vibration sensor according to an embodiment of the present disclosure to explain vibration information.

FIG. 2 is a graph showing waveforms measured by a vibration sensor to explain vibration information.

Referring to FIG. 2, for example, the vibration information may include at least one of a vibration frequency, an amplitude, and a waveform.

Further, referring to FIG. 1, the present implant osseointegration measuring apparatus includes a control unit 5. The control unit 5 determines the degree of osseointegration based on the measured vibration information.

For example, the control unit 5 may determine the degree of osseointegration by comparing vibration information of the implant fixture 9 which has been measured for each of the multiple vibrations with frequencies in different bands, respectively, with vibration information of the implant fixture 9 under no load.

Herein, the vibration information of the implant fixture 9 under no load may refer to vibration information in a state where the degree of osseointegration of the implant fixture 9 is 0. In other words, the implant fixture 9 under no load may refer to the implant fixture 9 in a state where any load (external force, reaction force, bearing power, etc.) is not applied by other components to the implant fixture 9 except the vibrations from the vibration generation unit 1. For example, the vibration information under no load may refer to vibration information in a state where the implant fixture 9 is not connected or not in contact with any component other than the vibration generation unit 1 before being inserted into the alveolar bone 0.

For example, referring to FIG. 2, it can be seen that the degree of osseointegration increases, a waveform caused by the vibrations of the implant fixture 9 has a smaller amplitude.

As such, vibration information of the osseointegrated implant fixture 9 has differences (e.g., a change in number of vibration, a change in amplitude, a difference in degree of signal distortion, etc.) from the vibration information of the implant fixture 9 under no load, and, thus, the control unit 5 may determine the degree of osseointegration by comparing the vibration information of the inserted implant fixture 9 with the vibration information of the implant fixture 9 under no load.

Further, the control unit 5 may determine the degree of osseointegration by comparing the vibration information of the implant fixture 9 which has been measured for each of the multiple vibrations with frequencies in different bands, respectively, with vibration information of the implant fixture 9 determined to be osseointegrated.

For example, as the measured vibration information of the implant fixture 9 is closer to the vibration information of the implant fixture 9 determined to be osseointegrated, the degree of osseointegration may be increased. Therefore, the control unit 5 may determine the degree of osseointegration by comparing the measured vibration information of the implant fixture 9 with the vibration information of the implant fixture 9 determined to be osseointegrated.

That is, the control unit 5 may determine the degree of osseointegration by comparing the measured vibration information of the inserted implant fixture 9 which has been measured for the multiple vibrations with frequencies in different bands, respectively, with at least one of the vibration information of the implant fixture 9 under no load and the vibration information of the implant fixture 9 determined to be osseointegrated.

Furthermore, the control unit 5 may identify and determine the degree of osseointegration for each of the three axes based on the three-axis vibration information. Therefore, it is possible to provide medical treatments necessary for the respective three axes. For example, if the degree of osseointegration for each of the three axes is determined and the degree of osseointegration for any one of the three axes is found lower than a reference degree of osseointegration (e.g., the degree of osseointegration required to fix the implant fixture 9 to an artificial tooth), it is possible to take appropriate measures to enhance the degree of osseointegration for the axis.

Moreover, the control unit 5 may determine the degree of osseointegration based on vibration information of one of the three axes with at least one of the highest vibration frequency and the highest amplitude. For example, the control unit 5 may determine the degree of osseointegration by comparing the vibration information of one of the three axes with at least one of the highest vibration frequency and the highest amplitude with vibration information of the axis under no load.

Accordingly, the degree of osseointegration can be determined by comparing vibration information of an axis with the highest vibration with vibration information of the axis under no load, and, thus, the accuracy of the determined degree of osseointegration can be improved. If the degree of osseointegration is determined by comparing vibration information of an axis with a low vibration with vibration information of the axis under no load, the determined degree of osseointegration may have a wide error range. The present implant osseointegration measuring apparatus determines the degree of osseointegration by comparing vibration information of one of the three axes with the highest vibration with vibration information of the axis under no load and thus can minimize the error range for the determined degree of osseointegration.

Further, the control unit 5 may set a vibration frequency and an intensity for the vibrations from the vibration generation unit 1.

Furthermore, the present implant osseointegration measuring apparatus may include a display unit configured to display relevant information such as the determined degree of osseointegration.

Moreover, the degree of osseointegration determined by the control unit 5 may be displayed as implant stability quotient (ISQ) ranging from 1 to 100.

Hereinafter, a method for measuring implant osseointegration according to an embodiment of the present disclosure (hereinafter, referred to as "the present implant osseointegration measuring method") using the above-described apparatus for measuring implant osseointegration according to an embodiment of the present disclosure will be described. However, components identical or similar to those explained above in the apparatus for measuring implant osseointegration according to an embodiment of the present disclosure will be assigned identical reference numerals, and explanation thereof will be briefly provided or omitted.

FIG. 3 is a schematic flowchart provided to explain the present implant osseointegration measuring method.

Referring to FIG. 3, the present implant osseointegration measuring method includes applying, by the vibration generation unit 1, multiple vibrations with frequencies in different bands, respectively, to the implant fixture 9 (S100).

In the process S100, the multiple vibrations with frequencies in different bands, respectively, may be low-frequency vibrations, medium-frequency vibrations, and high-frequency vibrations. For example, the low-frequency vibrations may be vibrations with frequencies of from 1,200 rpm to 3,600 rpm. Further, the medium-frequency vibrations may be vibrations with frequencies of from 4,200 rpm to 12,000 rpm. Furthermore, the high-frequency vibrations may be vibrations with frequencies of from 15,000 rpm to 24,000 rpm.

Further, referring to FIG. 3, the present implant osseointegration measuring method includes measuring, by the vibration sensor 3, three-axis vibration information of the implant fixture 9 caused by the vibrations from the vibration generation unit 1 (S300).

In the process S300, the vibration information may include at least one of a vibration frequency, an amplitude, and a waveform.

Referring to FIG. 3, the present implant osseointegration measuring method includes determining, by the control unit 5, the degree of osseointegration based on the measured vibration information (S500).

For example, in the process S500, the control unit 5 may determine the degree of osseointegration by comparing vibration information of the implant fixture 9 which has been measured for each of the multiple vibrations with frequencies in different bands, respectively, with vibration information of the implant fixture 9 under no load.

Further, in the process S500, the control unit 5 may determine the degree of osseointegration by comparing the vibration information of the implant fixture 9 which has been measured for each of the multiple vibrations with frequencies in different bands, respectively, with vibration information of the implant fixture 9 determined to be osseointegrated.

Furthermore, in the process S500, the control unit 5 may identify and determine the degree of osseointegration for each of the three axes based on the three-axis vibration information.

Moreover, in the process S500, the control unit 5 may determine the degree of osseointegration based on vibration information of one of the three axes with at least one of the highest vibration frequency and the highest amplitude.

Further, the present implant osseointegration measuring method may include installing the vibration generation unit 1 in the implant fixture 9 before the process S100. In the process of installing the vibration generation unit 1 in the implant fixture 9, the vibration generation unit 1 may be installed in an exposed portion of the implant fixture 9 inserted into the alveolar bone 0.

Furthermore, the present implant osseointegration measuring method may include removing the vibration generation unit from the implant fixture after the process S500.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. An apparatus for measuring implant osseointegration, comprising:
    a vibration generation unit configured to apply a vibration to an implant fixture attached to the vibration generation unit before being inserted into an alveolar bone, and to an implanted fixture which is inserted into the alveolar bone and to which the vibration generation unit is attached, respectively, wherein the vibration includes: a low-frequency vibration having a frequency from 1,200 rpm to 3,600 rpm, a medium-frequency vibration having a frequency from 4,200 rpm to 12,000 rpm, and a high-frequency vibration having a frequency from 15,000 rpm to 24,000 rpm;

a vibration sensor configured to measure a first three-axis vibration information from the implant fixture before being inserted into the alveolar bone, and a second three-axis vibration information from the implanted fixture inserted into the alveolar bone while applying the vibration thereto, respectively, wherein the first three-axis vibration information and the second three-axis information include: an x-axis vibration information, a y-axis vibration information and a z-axis vibration information, respectively; and a control unit configured to compare the first three-axis vibration information with the second vibration information with respect to each of the x-axis vibration information, the y-axis vibration information and the z-axis vibration information and determine a degree of osseointegration based on the comparison result, wherein the control unit is further configured to compare the determined degree of osseointegration with a reference degree of osseointegration, the reference degree of osseointegration being defined by a degree of osseointegration required to fix an artificial tooth to the implanted fixture.

2. The apparatus for measuring implant osseointegration of claim 1, wherein the comparison result includes: at least one of a difference in vibration frequencies, a difference in vibration amplitudes and a difference in vibration wave forms.

3. The apparatus for measuring implant osseointegration of claim 1, wherein the vibration generation unit is configured to be attached to and detached from an exposed portion of the implant fixture inserted into the alveolar bone.

4. A method for measuring implant osseointegration, comprising:

applying, by a vibration generation unit, a vibration to an implant fixture attached to the vibration generation unit before being inserted into an alveolar bone and, and to an implanted fixture which is inserted into the alveolar bone and to which the vibration generation unit is attached, respectively, wherein the vibration includes: a low-frequency vibration having a frequency from 1,200 rpm to 3,600 rpm, a medium-frequency vibration having a frequency from 4,200 rpm to 12,000 rpm, and a high-frequency vibration having a frequency from 15,000 rpm to 24,000 rpm;

measuring, by a vibration sensor, a first three-axis vibration information from the implant fixture before being inserted into the alveolar bone and a second three-axis vibration information from the implanted fixture inserted into the alveolar bone while applying the vibration thereto, respectively, wherein the first three-axis vibration information and the second three-axis information include:

an x-axis vibration information, a y-axis vibration information and a z-axis vibration information, respectively;

comparing, by a control unit, the first three-axis vibration information with the second three-axis vibration information with respect to each of the x-axis vibration information, the y-axis vibration information and the z-axis vibration information;

determining a degree of osseointegration based on the comparison result; and comparing the determined degree of osseointegration with a reference degree of osseointegration, the reference degree of osseointegration being defined by a degree of osseointegration required to fix an artificial tooth to the implanted fixture.

5. The method for measuring implant osseointegration of claim 4, wherein the comparison result includes: at least one of a difference in vibration frequencies, a difference in vibration amplitudes and a difference in vibration wave forms.

6. The method for measuring implant osseointegration of claim 4, wherein the applying comprises: attaching the vibration generation unit to an exposed portion of the implanted fixture inserted into the alveolar bone.

* * * * *